United States Patent
Yang (12)

(10) Patent No.: US 6,228,386 B1
(45) Date of Patent: May 8, 2001

(54) COMPOSITIONS AND METHODS TO REPAIR OSSEOUS DEFECTS

(75) Inventor: Shih-Liang S. Yang, Laguna Hills, CA (US)

(73) Assignee: Unicare Biomedical, Inc.

( * ) Notice: Subject to any disclaimer, the term of this patent is extended or adjusted under 35 U.S.C. 154(b) by 0 days.

(21) Appl. No.: 09/298,683

(22) Filed: Apr. 23, 1999

(51) Int. Cl.$^7$ ........................................ A61F 2/02
(52) U.S. Cl. .................. 424/426; 523/114; 523/115; 523/116; 623/16
(58) Field of Search ............. 424/426; 523/114, 523/115, 116; 623/16

(56) References Cited

U.S. PATENT DOCUMENTS

| | | |
|---|---|---|
| 3,905,047 | 9/1975 | Long . |
| 3,981,736 | 9/1976 | Broemer et al. . |
| 4,131,597 | 12/1978 | Bluethgen et al. . |
| 4,159,358 | 6/1979 | Hench et al. . |
| 4,239,113 | 12/1980 | Gross et al. . |
| 4,563,350 | 1/1986 | Nathan et al. . |
| 4,608,350 | 8/1986 | Howard, Jr. . |
| 4,786,555 | 11/1988 | Howard, Jr. . |
| 4,851,046 | 7/1989 | Low et al. . |
| 5,141,511 | 8/1992 | Bauer . |
| 5,204,106 | 4/1993 | Schepers et al. . |
| 5,658,332 | 8/1997 | Ducheyne et al. . |

FOREIGN PATENT DOCUMENTS

| | | |
|---|---|---|
| 0 112 319 B1 | 12/1982 | (EP) . |
| 0 145 210 A2 | 10/1983 | (EP) . |
| 0 206 726 A2 | 6/1985 | (EP) . |
| 0 206 726 B1 | 6/1985 | (EP) . |
| 0 206 726B2 | 6/1985 | (EP) . |
| 0 263 489B1 | 10/1986 | (EP) . |
| 0 382 047B1 | 2/1989 | (EP) . |
| 0 394 152A1 | 4/1989 | (EP) . |
| 0 394 152B1 | 4/1989 | (EP) . |
| WO 96/000536 | 6/1994 | (WO) . |

OTHER PUBLICATIONS

*Bioactive Ceramics: Theory & Applications,* L. L. Hench. In Bioceramics, vol. 7. (Proceedings of the 7th Internat'l. Symposium on Ceramics in Medicine, Turku, Finland 7/94).
*Clinical Applications of Bioglass Implants,* J. Wilson et al. In Bioceramics, vol. 7. (Proceedings of the 7th Internat'l. Symposium on Ceramics in Medicine, Turku, Finland 7/94).
*Bioactive Materials: The Potential for Tissue Regeneration,* Larry L. Hench at Society for Biomaterials 24th Annual Meeting, Apr. 22–26, 1998, San Diego, CA.
*Bonding of Soft Tissues to Bioglass,* J. Wilson & D. Nolletti, CRC Handbook of Bioactive Ceramics, vol. 1, pp. 283–302.
*In–Vivo Study of the Degradation of 4 Different–Composition Active Glasses,* A. M. Gatti, et al. In Bioceramics vol. 8, pp. 41–46.
*Healing of Periodontal Ligament after Implantation of Bioactive Glass in Surgically Created Periodontal Defects: A Pilot Study,* A. M. Gatti, et al. In Bioceramics vol. 7. (Proceedings of the 7th Internat'l. Symposium on Ceramics in Medicine, Turku, Finland, 7/94).
*Bone Growth into Spaces Between 45S5 Bioglass Granules,* H. Oonishi et al. In Bioceramics vol. 7. (Proceedings of the 7th Internat'l. Symposium on Ceramics in Medicine, Turku, Finland, 7/94).
*Effect of Surface Area to Volume Ratio on Vitro Surface Reactions of Bioactive Glass Particulates,* D.C. Greenspan et al. In Bioceramics, vol. 7. (Proceedings of the 7th Internat'l. Symposium on Ceramics in Medicine, Turku, Finland, 7/94).

*Primary Examiner*—Carlos A. Azpuru
(74) *Attorney, Agent, or Firm*—Stout, Uxa, Buyan & Mullins, LLP; Frank J. Uxa

(57) ABSTRACT

Compositions useful for repairing osseous defects include particulate bioactive and biocompatible glass including 40 to 58% by weight silica, 10 to 320 by weight calcia, 10 to 320 by weight soda and 2 to 10% by weight phosphorus pentoxide. The particles have a size distribution of: 20 to 65% by weight, 50 microns to less than 297 microns; 20 to 45% by weight, 297 to less than 350 microns; and 15 to 40% by weight, 350 microns to less than 420 microns. Methods for repairing osseous defects utilizing such compositions are also provided.

25 Claims, No Drawings

COMPOSITIONS AND METHODS TO REPAIR OSSEOUS DEFECTS

BACKGROUND OF THE INVENTION

The present invention relates to compositions and methods useful to repair osseous defects, for example, in various parts of the body of a human or animal. More particularly, the invention relates to compositions including, and methods using such compositions, bioactive, biocompatible glass particles having defined chemical make-ups and particle size distributions which provide substantial osseous defect repair benefits and substantial cost benefits.

Glass particles have previously been suggested for repairing osseous defects. For example, Low et al U.S. Pat. No. 4,851,046 discloses using glass particles having a broad size distribution of 90 to 710 microns to repair periodontal osseous defects. This patent discloses that a mixture of glass particles having a larger or wider particle size range, including particles having a size range of 500 to 710 microns, might produce a clinically more desirable product. This patent discloses glass particle compositions having a wide overall size distribution and including particles of 500 to 710 microns in size.

Schepers et al U.S. Pat. No. 5,204,106 discloses compositions of glass particles at least 95% by weight of which have sizes between 280 and 425 microns for use in a process for filling an osseous defect or deficiency. This narrow particle size distribution adversely impacts the cost of the product. Moreover, this patent make clear that if the particles are too small, that is smaller than 280 microns, the particles have a tendency to break, and if these particles are present in excessive amounts, that is 5% or more by weight, the desired performance is not achieved. Thus, although the narrow particle size composition is more costly, this patent concludes that such narrow size distribution provides enhanced performance benefits.

Ducheyne et al U.S. Pat. No. 5,658,332 discloses methods for forming osseous tissue in defect sites in the appendicular skeleton or in sites exhibiting reduced metabolic state using glass particles having a size from 200 to 300 microns. This narrow particle size distribution, which is even more narrow than that disclosed in the above-noted Schepers et al patent, disadvantageously increases the cost of the product.

It would be advantageous to provide a product which is effective in repairing osseous defects, meaning to include osseous deficiencies as well, and which is cost effective to produce and use.

SUMMARY OF THE INVENTION

New compositions and methods useful to repair osseous defects have been discovered. Such compositions provide performance benefits, for example, in terms of effectiveness in repairing osseous defects and/or in being able to be effectively handled or manipulated prior to such use relative to many of the prior art compositions. In addition, since the present compositions have a relatively broad particle size distribution range, the present compositions are cost effective to produce and use, often more cost effective to produce and use relative to prior art compositions. Moreover, the present compositions can be easily produced and used, for example, employing conventional techniques which are well known in the art.

In one broad aspect of the present invention, compositions useful to repair osseous defects are provided and consist essentially of particulate bioactive and biocompatible glass. The present glass particles have the following chemical make-up:

| | |
|---|---|
| Silica | 40 to 58% by weight |
| Calcia | 10 to 32% by weight |
| Soda | 10 to 32% by weight |
| Phosphorus pentoxide | 2 to 10% by weight |

In addition, the particles have the following size distribution:

| | |
|---|---|
| 53 microns to less than 297 microns | 20% to 65% by weight |
| 297 microns to less than 350 microns | 20% to 45% by weight |
| 350 microns to less than 420 microns | 15% to 40% by weight |

The particle size distributions set forth herein are based on a measurement using calibrated sieves.

The relatively broad particle size distribution of small and intermediate sized particles, in accordance with the present invention, has been found to provide very effective osseous defect repair, to be easily handled or manipulated during use, and to be cost effective to produce, for example, when compared to the compositions of the prior art, as described elsewhere herein. Such findings are indeed surprising since such prior art is directed to compositions which include a broad particle size distribution including particles of 500 to 710 microns in size, or to compositions which include very narrow particle size distributions. The present compositions are different from these prior art compositions, and provide benefits which are substantial and unexpected from the prior art.

Any and all features described herein and combinations of such features are included within the scope of the present invention provided that the features of any such combination are not mutually inconsistent.

These and other aspects and advantages of the present invention are apparent in the following detailed description and claims.

DETAILED DESCRIPTION OF THE INVENTION

The present compositions include bioactive and biocompatible glass particles including a combination of silica ($SiO_2$), calcia (Cao), soda ($Na_2O$) and phosphorus pentoxide ($P_2O_5$). Further, such particles have particles size distribution ranging from 53 microns to 420 microns or more.

As noted previously, in one broad aspect of the invention, the particulate bioactive and biocompatible glass has the following chemical make-up:

| | |
|---|---|
| Silica | 40 to 58% by weight |
| Calcia | 10 to 32% by weight |
| Soda | 10 to 32% by weight |
| Phosphorus pentoxide | 2 to 10% by weight | and the following particle size distribution:

| | |
|---|---|
| 53 microns to less than 297 microns | 20% to 65% by weight |
| 297 microns to less than 350 microns | 20% to 45% by weight |
| 350 microns to less than 420 microns | 15% to 40% by weight |

Measuring particle size distributions using calibrated sieves may result in a limited degree of variation. For example, the sizes of glass particles in the present compositions may vary by an amount of ±1% or less, or ±3% or ±4% or even ±6% of the nominal particle size. Such variations in the nominal sizes of the glass particles of the present compositions are within the scope of the present invention.

In one embodiment, the amount of particles from 53 microns to less than 297 microns is 20% to 50% by weight.

The present compositions have been found to be very effective in repairing osseous tissue defects (and deficiencies), for example, by implanting the present compositions in such defects.

The present compositions provide for effective bone fill in the osseous defects filled with the compositions. In addition, the speed of bone fill in the defects filled with the present compositions is increased relative to various prior art compositions. Further, more excavations are apparent in the particles of the present compositions, for example, relative to many of the prior art compositions. As used herein, the term "excavation" is defined as the formation of a central cavity through the interior of a particle at the time of full reaction of the particle which includes gelation and calcium phosphate layer formation. Excavation is evident by observation of cells within a particle. Excavations in a composition are advantageous, for example, to increase the amount of bone fill and the speed of bone fill in an osseous defect implanted with the composition.

The chemical make-up of the glass and/or the particle size distribution may be varied in accordance with the present invention to advantageously provide benefits in the specific application in which the present compositions are used. Such compositions, in generally, can be characterized as including small and intermediate sized particles which are often more effective in repairing osseous defects relative to prior art compositions and which are often more cost effective to produce relative to prior art compositions.

Preferably, the glass of the present compositions has the following chemical make-up:

| Silica | 42 to 54% by weight |
|---|---|
| Calcia | 15 to 29% by weight |
| Soda | 14 to 30% by weight |
| Phosphorus pentoxide | 2 to 8% by weight |

More preferably, the glass has the following chemical make-up:

| Silica | 42 to 48% by weight |
|---|---|
| Calcia | 20 to 29% by weight |
| Soda | 20 to 28% by weight |
| Phosphorus pentoxide | 3 to 8% by weight |

Still more preferably, the glass has the following chemical make-up:

| Silica | 44 to 46% by weight |
|---|---|
| Calcia | 23 to 26% by weight |
| Soda | 23 to 26% by weight |
| Phosphorus pentoxide | 5 to 7% by weight |

An especially useful glass for use in the present compositions is known as 45S5 and has the following chemical make-up:

| Silica | 45% by weight |
|---|---|
| Calcia | 24% by weight |
| Soda | 25% by weight |
| Phosphorus Pentoxide | 6% by weight |

All of the chemical make-ups disclosed herein, that is each of the percentages of individual components present, are within ±1%.

The presence of trace amounts of certain elements may affect the performance of the present compositions in osseous defect repair applications. For example, trace amounts of certain entities, such as aluminum ion, may prevent the formation of a hydroxy apatite (HA) gel layer on the particle surface. The formation of such a HA layer is believed to be a prerequisite for bone bonding to occur. Also, certain components, such as ferric oxide ($Fe_2O_3$), may cause the particles to disadvantageously discolor by gamma radiation.

Preferably the trace element concentrations of the present compositions are controlled within relatively stringent limits. In particular, in the present invention no single element, other than these included in the major or primary components of the glasses set forth herein, should be present in the glasses at concentrations of greater than about 0.2% by weight. Thus, it is preferred that the magnesia (MgO) content of the glass be less than about 0.2% by weight, the potassium oxide ($K_2O$) content be less than 0.2% by weight and the silver oxide (KgO) content be less than 0.2% by weight. In addition, the amounts of ferric oxide and alumina are less than about 0.02% and about 0.12% by weight, respectively.

The present compositions preferably include particulate glass including the following sized particles:

| 53 microns to less than 105 microns | 0% to 40% by weight |
|---|---|
| 105 microns to less than 210 microns | 0% to 40% by weight |
| 210 microns to less than 297 microns | 20% to 50% by weight |

More preferably, the amount of particles from 210 microns to less than 297 microns is in the range of 20 to 45% by weight. In one embodiment, the amount of particles from 210 to less than 250 microns is 10 to 25% by weight or 10 to 20% by weight, and the amount of particles from 250 microns to less than 297 microns is 10 to 30% by weight.

The particulate glass may, and preferably does, include substantially no particles less than 105 microns in size, more preferably substantially no particles less than 210 microns in size.

In a very useful embodiment, the amount of particles from 297 microns to less than 350 microns is 25 to 40% by weight. More preferably, the amount of particles from 297 microns to less than 350 microns is 28 to 36% by weight.

Preferably, 20% to about 40% by weight of the particles have a particle size from 350 microns to less than 420 microns. More preferably, 25 to 35% by weight of the particles have a size from 350 microns to less than 420 microns.

The particulate glass may, and preferably does, include substantially no particles more than 420 microns in size.

Very useful compositions in accordance with the present invention consist essentially of particulate bioactive and biocompatible glass having the following chemical make-up:

| | |
|---|---|
| Silica | 42 to 54% by weight |
| Calcia | 15 to 29% by weight |
| Soda | 14 to 30% by weight |
| Phosphorus pentoxide | 2 to 8% by weight | and the following particle size distribution:

| | |
|---|---|
| 53 microns to less than 297 microns | 20% to 50% by weight |
| 297 microns to less than 350 microns | 25% to 40% by weight |
| 350 microns to less than 420 microns | 20% to 40% by weight |

Preferably, the particulate glass includes substantially no particles less than 105 microns in size or substantially no particles less than 210 microns in size and substantially no particles more than 420 microns in size.

In a further useful embodiment, compositions in accordance with the present invention consist essentially of particulate bioactive and biocompatible glass having the following chemical make-up:

| | |
|---|---|
| Silica | 44 to 46% by weight |
| Calcia | 23 to 26% by weight |
| Soda | 23 to 26% by weight |
| Phosphorus pentoxide | 5 to 7% by weight | and the following particle size distribution:

| | |
|---|---|
| 53 microns to less than 297 microns | 20% to 50% by weight |
| 297 microns to less than 350 microns | 28% to 36% by weight |
| 350 microns to less than 420 microns | 25% to 35% by weight |

The present bioactive, biocompatible glass particles are prepared by melting together the various ingredients. For example, a mixture of powders is prepared including silica, calcium oxide and/or a calcium oxide precursor, a carbonate and/or other sodium oxide precursor for introducing at least a portion of the sodium content, and a phosphate and/or acid phosphate, for example, $CaHPO_4$, for introducing $P_2O_5$. This mixture is blended and melted, and the molten mixture is poured into liquid water which provides a solidified glass frit.

This glass frit is then ground into particles of approximately the proper size. Using calibrated sieves, for example, in accordance with ASTM method C429-65, the final composition is prepared. The various particle sizes identified herein correspond to specific mesh sizes, for example, as shown in the following:

| Particles size, microns | Sieve size, U.S. mesh |
|---|---|
| 53 | 270 |
| 105 | 140 |
| 210 | 70 |
| 250 | 60 |
| 297 | 50 |
| 350 | 45 |
| 420 | 40 |
| 500 | 35 |
| 710 | 25 |

One advantage of the present invention is that a relatively broad range of small and intermediate sized particles are employed in the final compositions. Therefore, the process for producing the present compositions can be specifically designed to achieve a relatively high yield of properly sized particles. In addition, larger sized particles can be recycled to the grinding operation to provide additional particles of the proper size. Overall, a relatively high percentage of the total glass frit produced is ground into properly sized particles for inclusion in the present composition. This reduces the overall cost of the present compositions.

The present compositions may be combined with a liquid medium, such as saline, whole blood or blood components, to make a slurry or paste which is highly suited for use in repairing osseous defects.

The present invention includes methods for repairing osseous defects, preferably including forming osseous tissue. Such methods comprise implanting a composition in accordance with the present invention in an osseous defect in an amount sufficient to repair such defect. Preferably, such implantation provides, over a period of time, for example, in the range of about 2 weeks to about 3 months or more, for the formation of osseous tissue at the defect site.

Osseous defects which can be repaired using the present compositions include, but are not limited to, cystic defect repairs, tumor or other lesion sites after resection, bone loss defects, fracture sites including delayed or non-union sites, joint repair sites, osteoporosis-related defects, periodontal defects, other defect sites in the appendicular skeleton and the like.

The following non-limiting example illustrates certain aspects of the present invention.

EXAMPLE 1

A series of four (4) particulate compositions are selected for testing. Each of the compositions includes particles of bioactive, biocompatible glass having the same chemical make-up as follows:

| | |
|---|---|
| Silica | 45% by weight |
| Calcia | 24.5% by weight |
| Soda | 24.5% by weight |
| Phosphorus pentoxide | 6% by weight |

Each of these compositions has a particle size distribution, determined by calibrated sieves, as follows:

Composition A 210 microns to less than 250 microns—13% by weight 250 microns to less than 297 microns—25% by weight 297 microns to less than 350 microns—32% by weight 350 microns to less than 420 microns—29% by weight Composition B About 210 microns to less than about 300 microns—100% by weight Composition C About 300 microns to less than about 350 microns—100% by weight Composition D About 90 microns to less than about 710 microns—100% by weight Mature New Zealand white rabbits are implanted with Compositions A to D. Two circular defects of 3 millimeters (mm) in diameter are placed in each ilium of the rabbits. The defects are enlarged gradually to a final diameter of 6 mm and filled with particles of one of the Compositions. Each defect is implanted with material of a singular, randomly selected Composition. Prior to being implanted, the Compositions are wet with three or four drops of sterile physiological saline on a dish. The Compositions are carried from the dish with a flat end spatula and placed in the defect site. All four Compositions form a cohesive mass upon wetting with saline and can be transferred using a spatula with ease. Each rabbit is implanted with all four Compositions. Two rabbits are sacrificed at 3 weeks and at 6 weeks after implantation for histological examination of the repair site.

Block sections of the ilia are excised and embedded in polymethyl methacrylate (PMMA) resin. Four serial sections are obtained from near the center of each defect. The section is stained for observation of the bone, fibrous tissue and glass. The amount of particles exhibiting excavation and the amount of bone fill found in each section are measured using a conventional light microscopy method. The data are compared and rated for each Composition.

Table 1 presents the data from the above study.

TABLE 1

Results of rabbit implantation study

| Rabbit ID | Implant Duration | Composition | Bone fill | Excavation |
|---|---|---|---|---|
| 1, 2 | 3 weeks | A | xxx | xx |
|  |  | B | xx | x |
|  |  | C | xx | x |
|  |  | D | xx | xx |
| 3, 4 | 6 weeks | A | xxxxxx | xxxx |
|  |  | B | xxxx | xxx |
|  |  | C | xxxx | xx |
|  |  | D | xxxxx | xxx |

There is more bone fill in the defects filled with Composition A than those filled with the other Compositions at both 3 weeks and 6 weeks after implantation. Moreover, the speed of bond fill is faster in the defects filled with Composition A than those filled with the other -Compositions. Also, more excavations are apparent in the particles of Composition A than in the particles of the other Compositions at 3 weeks and 6 weeks after implantation.

Table 2 compares the ease of manipulating the four Compositions.

TABLE 2

Ease of manipulation

| Composition | Ease of Manipulation | Cohesiveness with saline |
|---|---|---|
| A | Excellent | Excellent |
| B | Excellent | Excellent |
| C | Good | Good |
| D | Excellent | Excellent |

Composition D, which includes particles with a broad size distribution, appears to form a more compact and cohesive mass and is relatively easier to transport.

Composition A is found to be equivalent to or better than the other Compositions in terms of the ease of manipulation.

Clinically, the performance of bond graft materials may be measured by (1) the speed of bone fill and (2) the amount of bone fill. These, in turn, may be affected by (1) pouch formation, (2) packing density, (3) material formulation, (4) particle size, (5) surgical procedures and (6) patient condition.

This study shows that Composition A, in accordance with the present invention, performs as good as or better than the other Compositions, which are representative of prior art materials.

While this invention has been described with respect to various specific examples and embodiments, it is to be understood that the invention is not limited thereto and that it can be variously practiced within the scope of the following claims.

What is claimed is:

1. A composition useful to repair osseous defects, said composition consisting essentially of:

particulate bioactive and biocompatible glass having the following chemical make-up:

| Silica | 40 to 58% by weight |
|---|---|
| Calcia | 10 to 32% by weight |
| Soda | 10 to 32% by weight |
| Phosphorus pentoxide | 2 to 10% by weight | and the following particle size distribution:

| 53 microns to less than 297 microns | 20% to 65% by weight |
|---|---|
| 297 microns to less than 350 microns | 20% to 45% by weight |
| 350 microns to less than 420 microns | 15% to 40% by weight | the particle size distribution being measured using calibrated sieves.

2. The composition of claim 1 wherein the glass has the following chemical make-up:

| Silica | 42 to 54% by weight |
|---|---|
| Calcia | 15 to 29% by weight |
| Soda | 14 to 30% by weight |
| Phosphorus pentoxide | 2 to 8% by weight. |

3. The composition of claim 1 wherein the glass has the following chemical make-up:

| Silica | 42 to 48% by weight |
|---|---|
| Calcia | 20 to 29% by weight |
| Soda | 20 to 28% by weight |
| Phosphorus pentoxide | 3 to 8% by weight. |

4. The composition of claim 1 wherein the glass has the following chemical make-up:

| Silica | 44 to 46% by weight |
|---|---|
| Calcia | 23 to 26% by weight |
| Soda | 23 to 26% by weight |
| Phosphorus pentoxide | 5 to 7% by weight. |

5. The composition of claim 1 wherein the particulate glass includes the following sized particles:

| 53 microns to less than 105 microns | 0% to 40% by weight |
|---|---|
| 105 microns to less than 210 microns | 0% to 40% by weight |
| 210 microns to less than 297 microns | 20% to 50% by weight . |

6. The composition of claim 1 wherein the particulate glass includes the following sized particles:

| | |
|---|---|
| 53 microns to less than 105 microns | 0% to 40% by weight |
| 105 microns to less than 210 microns | 0% to 40% by weight |
| 210 microns to less than 297 microns | 20% to 45% by weight . |

7. The composition of claim 5 wherein the particulate glass includes the following sized particles:

210 microns to less than 250 microns 10% to 25% by weight.

8. The composition of claim 6 wherein the particulate glass includes the following sized particles:

210 microns to less than 250 microns 10% to 20% by weight.

9. The composition of claim 7 wherein the particulate glass includes substantially no particles less than 105 microns in size.

10. The composition of claim 8 wherein the particulate glass includes substantially no particles less than 210 microns in size.

11. The composition of claim 1 wherein the particulate glass has the following sized particles:

297 microns to less than 350 microns 25% to 40% by weight.

12. The composition of claim 1 wherein the particulate glass has the following sized particles: 297 microns to less than 350 microns 28% to 36% by weight.

13. The composition of claim 1 wherein the particulate glass has the following sized particles:

350 microns to less than 420 microns 20% to 40% by weight.

14. The composition of claim 1 wherein the particulate glass has the following sized particles:

350 microns to less than 420 microns 25% to 35% by weight.

15. The composition of claim 12 wherein the particulate glass includes substantially no particles more than 420 microns in size.

16. The composition of claim 14 wherein the particulate glass includes substantially no particles more than 420 microns in size.

17. A composition useful to repair osseous defects, said composition consisting essentially of:

particulate bioactive and biocompatible glass having the following chemical make-up:

| | |
|---|---|
| Silica | 42 to 54% by weight |
| Calcia | 15 to 29% by weight |
| Soda | 14 to 30% by weight |
| Phosphorus pentoxide | 2 to 8% by weight | and the following particle size distribution:

| | |
|---|---|
| 53 microns to less than 297 microns | 20% to 50% by weight |
| 297 microns to less than 350 microns | 25% to 40% by weight |
| 350 microns to less than 420 microns | 20% to 40% by weight | the particle size distribution being measured using calibrated sieves.

18. The composition of claim 17 wherein the particulate glass has the following sized particles:

210 microns to less than 250 microns 10% to 25% by weight.

19. The composition of claim 17 wherein the particulate glass includes substantially no particles more than 420 microns in size.

20. A composition useful to repair osseous defects, said composition consisting essentially of:

particulate bioactive and biocompatible glass having the following chemical make-up:

| | |
|---|---|
| Silica | 44 to 46% by weight |
| Calcia | 23 to 26% by weight |
| Soda | 23 to 26% by weight |
| Phosphorus pentoxide | 5 to 7% by weight | and the following particle size distribution:

| | |
|---|---|
| 53 microns to less than 297 microns | 20% to 50% by weight |
| 297 microns to less than 350 microns | 28% to 36% by weight |
| 350 microns to less than 420 microns | 25% to 35% by weight | the particle size distribution being measured using calibrated sieves.

21. The composition of claim 20 wherein the particulate glass has the following sized particles:

210 microns to less than 250 microns 10% to 25% by weight.

22. The composition of claim 20 wherein the particulate glass includes substantially no particles more than 420 microns in size.

23. A method of repairing an osseous defect comprising:

implanting an effective amount of the composition of claim 1 in an osseous defect.

24. A method of repairing an osseous defect comprising:

implanting an effective amount of the composition of claim 17 in an osseous defect.

25. A method of repairing an osseous defect comprising:

implanting an effective amount of the composition of claim 20 in an osseous defect.

* * * * *